United States Patent
Moradi et al.

(10) Patent No.: US 11,130,735 B2
(45) Date of Patent: Sep. 28, 2021

(54) PROCESS FOR THE PREPARATION OF FLUOPICOLIDE

(71) Applicant: Bayer Aktiengesellschaft, Leverkusen (DE)

(72) Inventors: Wahed Ahmed Moradi, Monheim (DE); Albert Schnatterer, Leverkusen (DE)

(73) Assignee: Bayer Aktiengesellschaft

( * ) Notice: Subject to any disclaimer, the term of this patent is extended or adjusted under 35 U.S.C. 154(b) by 0 days.

(21) Appl. No.: 16/765,763

(22) PCT Filed: Nov. 21, 2018

(86) PCT No.: PCT/EP2018/082011
§ 371 (c)(1),
(2) Date: May 20, 2020

(87) PCT Pub. No.: WO2019/101769
PCT Pub. Date: May 31, 2019

(65) Prior Publication Data
US 2020/0283388 A1    Sep. 10, 2020

(30) Foreign Application Priority Data
Nov. 22, 2017  (EP) ..................... 17203042

(51) Int. Cl.
*C07D 213/40*    (2006.01)
(52) U.S. Cl.
CPC ................... *C07D 213/40* (2013.01)
(58) Field of Classification Search
None
See application file for complete search history.

(56) References Cited

U.S. PATENT DOCUMENTS

| | | |
|---|---|---|
| 6,503,933 B1 | 1/2003 | Moloney et al. |
| 6,828,441 B2 | 12/2004 | Moloney et al. |
| 7,232,911 B2 | 6/2007 | Vangelisti et al. |
| 7,456,290 B2 | 11/2008 | Vangelisti |
| 2003/0171410 A1 | 9/2003 | Moloney et al. |
| 2006/0004206 A1 | 1/2006 | Vangelisti |
| 2006/0100441 A1 | 5/2006 | Vangelisti et al. |
| 2018/0297952 A1 | 10/2018 | Moradi et al. |

FOREIGN PATENT DOCUMENTS

| | | |
|---|---|---|
| EP | 1056723 B1 | 12/2000 |
| WO | 9942447 A1 | 8/1999 |
| WO | 0216322 A2 | 2/2002 |
| WO | 2004046114 A1 | 6/2004 |
| WO | 2004065359 A2 | 8/2004 |
| WO | 2016173998 A1 | 11/2016 |

OTHER PUBLICATIONS

Nerozzi, Team Leader at Johnson Matthey, Platinum Metals Review, vol. 56, (4), pp. 236-241 (Year: 2012).*
PCT International Search Report for PCT/EP2018/082011, dated Feb. 25, 2019.
Nishimura, Shigeo. "Handbook of heterogeneous catalytic hydrogenation for organic synthesis," New York etc: Wiley, 2001, pp. 259-285.

* cited by examiner

*Primary Examiner* — Zinna Northington Davis
(74) *Attorney, Agent, or Firm* — McBee Moore & Vanik, IP, LLC

(57) ABSTRACT

The present invention relates to an improved process for the preparation of substituted pyridylmethyl-benzamide derivatives of formula (I), in particular 2,6-Dichloro-N-{[3-chloro-5-(trifluoromethyl)-2-pyridyl]methyl}benzamide (Fluopicolide), from substituted 2-(Aminomethyl)pyridine derivatives which are obtained by Raney-Nickel hydrogenation.

13 Claims, No Drawings

PROCESS FOR THE PREPARATION OF FLUOPICOLIDE

CROSS-REFERENCE TO RELATED APPLICATIONS

This application is the National Stage entry of International Application No. PCT/EP2018/082011, filed 21 Nov. 2018, which claims priority to European Patent Application No. 17203042.1, filed 22 Nov. 2017.

BACKGROUND

Field

The present invention relates to an improved process for the preparation of substituted pyridylmethyl-benzamide derivatives of formula (I), in particular 2,6-Dichloro-N-{[3-chloro-5-(trifluoromethyl)-2-pyridyl]methyl}benzamide (Fluopicolide), from substituted 2-(Aminomethyl)pyridine derivatives which are obtained by Raney-Nickel hydrogenation.

Description of Related Art

Substituted pyridylmethylbenzamide derivatives of formula (I)

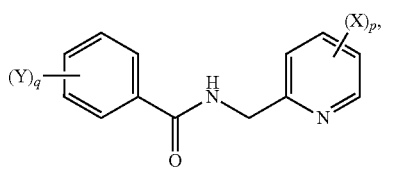

wherein
p is an integer equal to 1, 2, 3 or 4,
q is an integer equal to 1, 2, 3 or 4,
X is independently selected from the group consisting of hydrogen, halogen, $(C_1-C_4)$-alkyl and $(C_1-C_4)$-haloalkyl with the proviso that at least one X is halogen,
Y is halogen,
are highly active against phytopathogenic fungi. Compounds of formula (I) are described in EP1056723 B1.

Substituted 2-(Aminomethyl)pyridine derivatives, such as in particular 3-Chloro-2-cyano-5-trifluoro-methylpyridine, are important intermediates for the preparation of Fluopicolide (2,6-Dichloro-N-{[3-chloro-5-(trifluoromethyl)-2-pyridyl]methyl}benzamide), a commercially available fungicide, according to formula (Ia) shown below

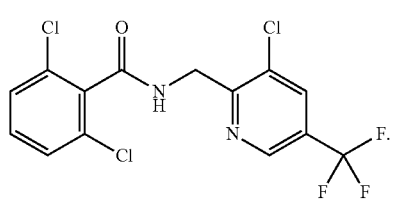

The preparation of substituted 2-(Aminomethyl)pyridine derivatives is known in the prior art. WO 99/42447 and WO 2004/65359 describe the formation of substituted pyridylmethylbenzamide derivatives via a substituted imine derivative. This process involves several steps and is thus not very efficient. WO 2002/016322 discloses the preparation of substituted 2-(Aminomethyl)pyridine derivatives by hydrogenation of the corresponding substituted 2-Cyanopyridine derivatives in the presence of palladium on chorcoral. However, this process bears several disadvantages such as low yield of the hydrogenation step, formation of dehalogenated side products, isolation of 2-(Amino-methyl)pyridine derivatives and stability issues with the isolated material. WO 2004/046114 discloses the catalytic hydrogenation of substituted 2-cyanopyridine derivatives to the corresponding 2-(Aminomethyl)pyridine derivatives in the presence of Raney-Nickel in acetic acid. In general the catalytic hydrogenation of nitriles is well known in the literature and can be carried out with different nickel catalysts (Nishimura in "Handbook of Heterogeneous Catalytic Hydrogenation for Organic Synthesis", pp. 259-285, John Wiley and Sons, New York, 2001). It is also known that the catalytic hydrogenation of nitriles to the desired primary amines is usually accompanied by the formation of significant amounts of secondary and tertiary amines which contaminate the desired primary amine and makes the isolation very complicated, costly and inefficient and thus not suitable for being used on an industrial scale. Surprisingly, the method described in WO 2004/046114 does not result in the formation of unwanted side products and thus is a good alternative to the processes disclosed in WO 99/42447, WO 2004/6535 and WO 2002/016322. However, the reduction of substituted 2-Cyanopyridine derivatives via hydrogenation in the presence of Raney-Nickel as described in WO 2004/046114 has the enormous drawback that the resulting 2-(Aminomethyl)pyridine derivatives as well as later the substituted pyridylmethylbenzamide derivatives are contaniminated with Nickel due to the so-called Nickel-leaching to an extent which is not acceptable for agricultural products. Thus, the described prior art processes are therefore not very well suitable for a large scale production. The method described in WO 99/42447 for the formation of substituted pyridylmethylbenzamide derivatives of formula (I) is not suitable for a large scale production.

SUMMARY

It is therefore an object of the present invention to provide a novel, improved, technically feasible, more economically and environmentally viable process suitable for industrial scale for preparing substituted pyridylmethylbenzamide derivatives from substituted 2-(Aminomethyl)pyridine derivatives which are obtained by Raney-Nickel hydrogenation.

The new process of the present invention, as described in detail hereinafter, provides an economic, technically easily feasible process which solves the above-mentioned issues of the processes described in the prior art and which is thus suitable for industrial scale for preparing substituted pyridylmethyl-benzamide derivatives with significantly reduced Nickel content from substituted 2-(Amino-methyl)pyridine derivatives which are obtained by Raney-Nickel hydrogenation.

The object of the present invention is a process
[A] for preparing substituted pyridylmethylbenzamide derivatives of the formula (I) or salts thereof,

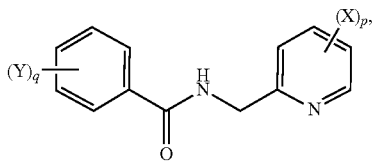

wherein
p is an integer equal to 1, 2, 3 or 4,
q is an integer equal to 1, 2, 3 or 4,
X is independently selected from the group consisting of hydrogen, halogen, $(C_1\text{-}C_4)$-alkyl and $(C_1C_4)$-haloalkyl with the proviso that at least one X is halogen,
Y is halogen,
characterized in that it comprises the following steps
[A1] reacting a substituted 2-(aminomethyl)pyridyl derivative according to formula (III) or salts thereof

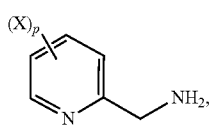

wherein p and X are defined as above, and
wherein the compound of formula (III) is obtained via a Raney-Nickel hydrogenation,
in a suitable solvent in the presence of a suitable base at a temperature from 0° C. to +50° C. with a compound of formula (IV)

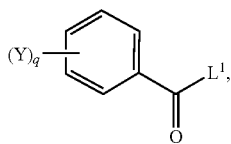

wherein
q is an integer equal to 1, 2, 3 or 4,
Y is halogen and
$L^1$ is a leaving group,
[A2] heating the resulting reaction mixture to a temperature from +70° C. to +90° C.,
[A3] acidifying the reaction mixture with a suitable acid to a pH value of 0 to 3,
[A4] separating the phases and discarding the aqueous phase,
[A5] adding water and a suitable base to adjust the pH value of 4 to 6,
[A6] separating the phases and discarding the aqueous phase,
[A7] cooling down the reaction mixture slowly to 0° C. to +10° C.
[A8] filtering the reaction mixture, washing the filter cake with a suitable solvent and drying the wet filter cake to yield a compound of formula (I) or salts thereof.

DETAILED DESCRIPTION OF A PREFERRED EMBODIMENT

In another embodiment process [A] comprises further steps [A4a] and [A4b] after step [A4]
wherein
[A4a] adding water and a suitable acid to adjust the pH value of 0 to 3,
[A4b] separating the phases and discarding the aqueous phase.

Unless otherwise stated, the following definitions apply for the substituents and residues used throughout this specification and claims.

The corresponding salts of the compounds according to formula (I) are preferably hydrogensulfates, sulfates, hydrogensulfate-sulfate mixtures, hydrochlorides, phosphates, formates, or acetates.

The corresponding salts of the compounds according to formula (III) are preferably hydrogensulfates, sulfates, hydrogensulfate-sulfate mixtures, hydrochlorides, phosphates, formates, or acetates. Particular preferably are acetates.

Throughout the invention the term equivalent refers to molar equivalents.

Alkyl represents a straight-chain or branched saturated hydrocarbon radical having 1 to 4 carbon atoms. Non-limiting examples include methyl, ethyl, propyl, 1-methylethyl (iso-propyl), n-butyl, 1-methylpropyl (iso-butyl), 2-methylpropyl (sec-butyl), 1,1-dimethylethyl (tert.-butyl). Preference is given to $(C_1\text{-}C_2)$-alkyl representing a straight-chain saturated hydrocarbon radical having 1 or 2 carbon atoms, such as methyl or ethyl.

Haloalkyl represents in general an alkyl-radical having 1 to 4 carbon atoms, in which 1 up to all hydrogen atoms are replaced by halogen atoms. Non-limiting examples include chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoro-methylbutyl. Preference is given to difluoromethyl, trifluoromethyl, dichloromethyl, trichloromethyl.

Preferably X is selected independently from the group consisting of fluoro, chloro, bromo, methyl, ethyl and $(C_1\text{-}C_2)$-haloalkyl having 1 to 5 halogen atoms independently selected from the group consisting of fluoro and chloro.

More preferably X is selected independently from the group consisting of fluoro, chloro, methyl, ethyl or $(C_1\text{-}C_2)$-haloalkyl having 1 to 5 halogen atoms independently selected from the group consisting of fluoro and chloro.

Particular preferably X is selected independently from the group consisting of fluoro, chloro, difluoromethyl, trifluoromethyl, dichloromethyl and trichloromethyl.

Very particular preferably X is selected independently from the group consisting of chloro and trifluoromethyl.

Particular preferably, the 2-pyridyl moiety is substituted by X in 3- and 5-position.

Very particular preferably the compound according to formula (III) is 1-[3-chloro-5-(trifluoromethyl)pyrid-2-yl-methanamine-acetate according to formula (IIIa)

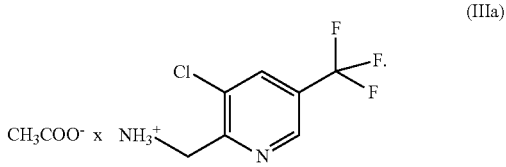 [SMILES: [NH3+]Cc1ncc(C(F)(F)F)cc1Cl]
(IIIa)

Preferably Y is selected independently from the group consisting of fluoro, chloro and bromo.

More preferably Y is selected independently from the group consisting of fluoro and chloro.

Particular preferably Y is chloro.

More preferably, the benzoyl moiety is substituted by X in 2- and 6-position.

Particular preferably the compound according to formula (IV) is 2,6-dichlorobenzoylchloride according to formula (IVa)

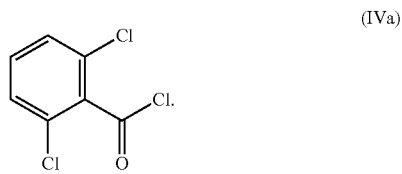 [SMILES: O=C(Cl)c1c(Cl)cccc1Cl]
(IVa)

Preferably p is an integer equal to 1, 2 or 3.
More preferably p is an integer equal to 1 or 2.
Particular preferably p is an integer equal to 2.
Preferably q is an integer equal to 1, 2 or 3.
More preferably q is an integer equal to 1 or 2.
Particular particular q is an integer equal to 2.
Preferably leaving group L' is halogen.
More preferably leaving group L' is selected from the group consisting of chloro, bromo and iodo.
Particular preferably leaving group L' is chloro.
Very particular preferably the compound according to formula (I) is Fluopicolide according to formula (Ia)

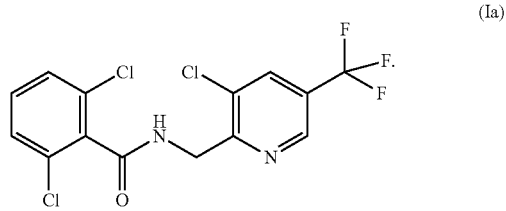 [SMILES: O=C(NCc1ncc(C(F)(F)F)cc1Cl)c1c(Cl)cccc1Cl]
(Ia)

Particular preferably an object of the present invention is a process [A] for the preparation of a substituted pyridylmethylbenzamide of formula (Ia)

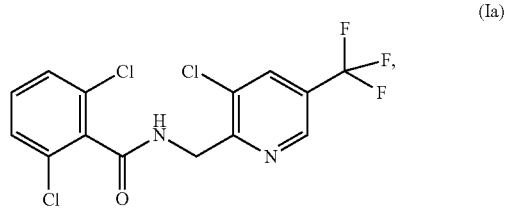 [SMILES: O=C(NCc1ncc(C(F)(F)F)cc1Cl)c1c(Cl)cccc1Cl]
(Ia)

characterized in that it comprises the following steps
[A1] reacting a substituted 2-(aminomethyl)pyridyl derivative according to formula (Ma)

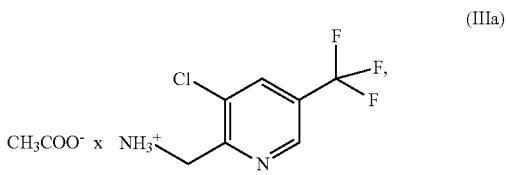 [SMILES: [NH3+]Cc1ncc(C(F)(F)F)cc1Cl]
(IIIa)

wherein the compound of formula (IIIa) is obtained via a Raney-Nickel hydrogenation,
in a suitable solvent in the presence of a suitable base at a temperature from 0° C. to +50° C. with a compound of formula (IVa)

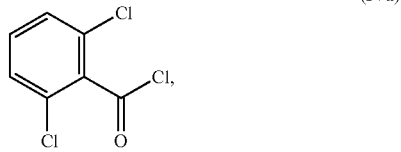
(IVa)

[A2] heating the resulting reaction mixture to a temperature from +70° C. to +90° C.,
[A3] acidifying the reaction mixture with a suitable acid to a pH value of 0 to 3,
[A4] separating the phases and discarding the aqueous phase,
[A5] adding water and a suitable base to adjust the pH value of 4 to 6,
[A6] separating the phases and discarding the aqueous phase,
[A7] cooling down the reaction mixture slowly to 0° C. to +10° C.
[A8] filtering the reaction mixture, washing the filter cake with a suitable solvent and drying the wet filter cake to yield a compound of formula (I) or salts thereof.

Very particular preferably process [A] comprises further steps [A4a] and [A4b] after step [A4]
wherein
[A4a] adding water and a suitable acid to adjust the pH value of 0 to 3,
[A4b] separating the phases and discarding the aqueous phase.

Suitable bases for step [A1] are selected from inorganic bases such sodium carbonate, sodium bicarbonate, potassium carbonate, potassium bicarbonate, sodium hydroxide, potassium hydroxide, calcium hydroxide, magnesium hydroxide or organic bases such as triethyl amine, N,N-diisopropylethylamine. Preferred bases for step [A1] are selected from sodium carbonate, potassium carbonate, sodium hydroxide, potassium hydroxide and calcium hydroxide. More preferred bases are selected from sodium hydroxide, potassium hydroxide and calcium hydroxide. Mostly preferred bases are selected from sodium hydroxide and potassium hydroxide. Preferably, in step [A1] a base as defined herein is added until adjustment of the pH value of pH 4 to 14 of the reaction solution, particular preferably of pH 6 to 9 is achieved.

Suitable solvents for the step [A1] are selected from alcohols such as methanol, ethanol, iso-propanol, propanol, n-butanol, iso-butanol, t-pentanol, benzyl alcohol, 1,3-butanediol, 1,4-butandiol, 2-butoxy-ethanol, cyclohexanol, diethylene glycol, diethylen glycol methyl ether, dipropylene glycol, dipropylene glycol methyl ether, 2-ethoxyethanol, ethylene glycol, glycerol, hexanole, hexylene glycol, isopentanol, isobutanol, 2-methoxyethanol, 1-octanol, pentanol, propylene glycol, tetraethylene glycol, triethylene glycol; from ethers such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, methyl cyclopenthylether, dioxane, dichlorodiethyl ether, petroleum ether, ligroin and polyethers of ethylene oxide and/or propylene oxide; from hydrocarbons such as toluene, xylenes, ethylbenzene, or from other solvents such as water or N,N-Dimethylacetimide, N,N-Dimethylformamide, 2-pyrrolidone and N-methyl pyrrolidone. Preferred solvents are selected from water and hydrocarbons such as toluene, xylenes and ethylbenzene and mixtures thereof in a ratio from 10:1 to 1:10. Particularly preferred is a mixture of water and toluene in a ratio of 1:1.

Preferably the reaction mixture in step [A2] is heated to a temperature from +70° C. to +90° C. for a time from 30 min to 3 hours.

More preferably the reaction mixture in step [A2] is heated to a temperature from +75° C. to +90° C. for a time from 1 hour to 3 hours.

More preferably the reaction mixture in step [A2] is heated to a temperature from +80° C. to +85° C. for a time from 30 min to 3 hours.

Even more preferably the reaction mixture in step [A2] is heated to a temperature from +80° C. to +85° C. for a time from 1 hour to 2 hours.

Suitable acids for steps [A3] and [A4a] are selected from inorganic acids such as gaseous hydrogen chloride, hydrochloric acid (HCl), sulfuric acid ($H_2SO_4$), phosphoric acid ($H_3PO_4$) or organic acids such as acetic acid ($CH_3CO_2H$), trifluoro acetic acid ($CF_3CO_2H$), citric acid, p-toluenesulfonic acid, methane-sulfonic acid, trifluoromethanesulfonic acid, formic acid. Preferred acids are selected from hydrochloric acid (HCl) and sulfuric acid ($H_2SO_4$). Preferably, in steps [A3] and [A4a] an acid as defined herein is added to the reaction mixture to adjust the pH value to pH 0 to 4, very preferably to a value of pH 0 to 3.

Suitable bases for step [A5] are selected from inorganic bases such sodium carbonate, sodium bicarbonate, potassium carbonate, potassium bicarbonate, sodium hydroxide, potassium hydroxide, calcium hydroxide, magnesium hydroxide or organic bases such as triethyl amine, N,N-diisopropylethylamine. Preferred bases for step [A5] are selected from sodium carbonate, potassium carbonate, sodium hydroxide, potassium hydroxide and calcium hydroxide. More preferred bases are selected from sodium hydroxide, potassium hydroxide and calcium hydroxide. Mostly preferred bases are selected from sodium hydroxide and potassium hydroxide. Preferably, in step [A5] a base as defined herein is added until adjustment of the pH value of the reaction solution to pH 4 to 7, particular preferably pH 5 to 6 is achieved.

The process according to the invention is suitable for large scale production due to its technical feasibility. Substituted 2-(Aminomethyl)pyridine derivatives are important intermediates for the production of pyridylmethylbenzamide derivatives of formula (I). The processes described in the prior art are not suitable for industrial scale production due to formation of side products, reagents used in the synthetis and/or residual amount of Nickel. Surprisingly, it has been found by following the process of the present invention an economic, technically easily feasible method is provided to use the substituted 2-(Aminomethyl)pyridine derivatives obtained via Raney-Nickel-catalyzed hydrogenation for the preparation of pyridylmethylbenzamide derivatives of formula (I) with significantly reduced Nickel content. Thus, the obtained pyridylmethylbenzamide derivatives of formula (I) are suitable for agricultural products.

METHODS AND ABREVIATIONS

Methods

Method 1 (HPLC): Instrument: Agilent 1100; column: Zorbax Eclipse XDB-C18 1.8µ, 50 mm×4.6 mm; eluent A: 1 L water+1 mL phosphoric acid, eluent B: acetonitrile; gradient: 0.0 min 90% A→4.25 min 5% A→6.0 min 5% A→6.01 min 90% A; column temperature: 55° C.; flow rate: 2.0 mL/min; UV detection: 210 nm.

Method 2 (atomic absorption spectrocopy): Gaphite furnace

Abbreviations

HPLC high pressure liquid chromatography wt. % weight percent

EXAMPLES

The examples shown below further illustrate the invention without limiting it.

Example 1

To a solution of 597.8 g 1-[3-Chloro-5-(trifluoromethyl) pyridin-2-yl]methanamine-Acetate (2.2 mol, 77.5 wt. % purity, Ni-content 480 ppm, prepared according to WO 2004/046114) in 1623 g water and 1623.5 g toluene 456.1 g 2,6-Dichlorobenzoylchloride (2.175 mol) were added at +20° C. and 282.3 g of an aqueous sodium hydroxide solution (32 wt. %) were dosed in parallel in 60 minutes. The internal temperature was kept between +38° C. and +43° C. The reaction was exotherm. The jacket temperature was kept between +30° C. and +45° C. After complete addition of 2,6-dichlorobenzoylchloride the suspension was allowed to proceed for another 10 minutes at +40° C. then the temperature was raised to +80° C. in 55 minutes. The thick suspension was stirred for another 15 minutes at +80° C. The pH value of the water phase was about 4.1. Afterwards 109.5 g hydrochloric acid (20 wt. %, 0.651 mol) were added at +80° C. to the suspension to adjust the pH to <1. The resulting biphasic solution was stirred for additional 5 minutes. After phase separation at +82° C. the aqueous phase was discharged and 176 g water were added to the organic phase. The pH of the water phase was about 1.42. Further 9.2 g hydrochloric acid (20 wt %) were added to adjust the pH to 0.8. After phase separation at 82° C. the aqueous phase was discharged and further 176.5 g water were added to the organic solution and 16.1 g of an aqueous sodium hydroxide solution (32 wt %, 0.129 mol) were added to adjust the pH to 5-5.5. After phase separation at +82° C. the aqueous phase was discharged. The solution was cooled down in 2 hours to 5° C. and stirred for 60 minutes. Crystallization starts at approximately +60° C. Finally the product was separated by filtration and the wet cake is washed with 224 g pre-cooled toluene (replacement wash) at +5° C. and the wet cake is dried under vacuum at +65° C. 810.50 g 2,6-dichloro-N-{[3-chloro-5-(trifluoromethyl)-2-pyridyl]methyl}benzamide (99.7 wt. %) with 95.71% chemical yield are obtained.

$R_t$(Method 1)=3.25 min
Nickel content (Method 2): below 0.5 ppm

The invention claimed is:

1. A process for preparing a substituted pyridylmethyl-benzamide compound of formula (I) or a salt thereof,

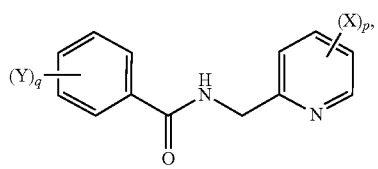

wherein
P is an integer equal to 1, 2, 3 or 4,
q is an integer equal to 1, 2, 3 or 4,
X is independently selected from the group consisting of hydrogen, halogen, ($C_1$-$C_4$)-alkyl and ($C_1$$C_4$)-haloalkyl with the proviso that at least one X is halogen,
Y is halogen,
comprising
[A1] reacting a substituted 2-(aminomethyl)pyridyl compound according to formula (III) and/or a salt thereof

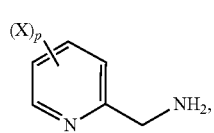

wherein p and X are defined as above, and
wherein the compound of formula (III) is obtained via a Raney-Nickel hydrogenation,
in a suitable solvent in the presence of a suitable base at a temperature from 0° C. to +50° C. with a compound of formula (IV)

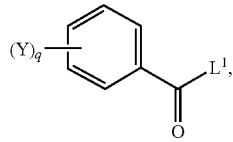

wherein
q is an integer equal to 1, 2, 3 or 4,
Y is halogen and
$L^1$ is a leaving group,
wherein the suitable solvent is selected from the group consisting of hydrocarbon and a mixture of water and hydrocarbon in a ratio from 10:1 to 1:10, and
wherein the suitable base is selected from the group consisting of sodium hydroxide and potassium hydroxide,
[A2] heating the resulting reaction mixture to a temperature from +70° C. to +90° C.,
[A3] acidifying the reaction mixture with a suitable acid to a pH value of 0 to 3,
[A4] separating the phases and discarding the aqueous phase,

[A5] adding water and a suitable base to adjust the pH value of 4 to 6,
[A6] separating the phases and discarding the aqueous phase,
[A7] cooling down the reaction mixture slowly to 0° C. to +10° C.
[A8] filtering the reaction mixture, washing the filter cake with a suitable solvent and drying the wet filter cake to yield a compound of formula (I) and/or a salt thereof.

2. A process according to claim 1, wherein the process further comprises [A4a] and [A4b] after [A4], as follows
[A4a] adding water and a suitable acid to adjust the pH value of 0 to 3,
[A4b] separating the phases and discarding the aqueous phase.

3. A process according to claim 1, wherein the suitable solvent in step [A1] is a mixture of water and hydrocarbon in a ratio from 10:1 to 1:10.

4. A process according to claim 1, wherein the suitable base in [A1] is sodium hydroxide.

5. A process according to claim 1, wherein the suitable base in [A1] is added until adjustment of the pH value of pH 6 to 9 of the reaction solution is achieved.

6. A process according to claim 1, wherein the suitable acid in [A3] is selected from the group consisting of hydrochloric acid (HCl) and sulfuric acid ($H_2SO_4$).

7. A process according to claim 2, wherein the suitable acid in [A4a] is selected from the group consisting of hydrochloric acid (HCl) and sulfuric acid ($H_2SO_4$).

8. A process according to claim 1, wherein the suitable base in [A5] is selected from the group consisting of sodium hydroxide, potassium hydroxide and calcium hydroxide.

9. A process according to claim 1, wherein the compound according to formula (I) is Fluopicolide according to formula (Ia)

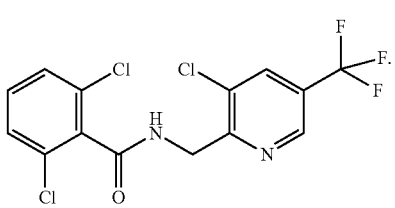

10. A process according to claim 1, wherein the compound according to formula (III) is 1-[3-chloro-5-(trifluoromethyl)pyrid-2-ylmethanamine-acetate according to formula (IIIa)

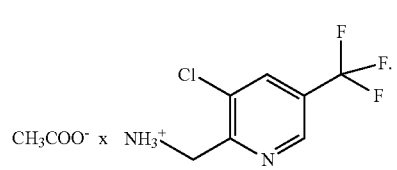

11. A process according to claim 1, wherein the compound according to formula (IV) is 2,6-dichlorobenzoylchloride according to formula (IVa)

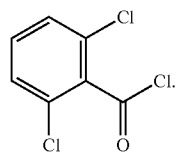
(IVa)
12. A process according to claim 1, wherein the hydrocarbon is selected from the group consisting of toluene, xylene and ethylbenzene.
13. A process according to claim 1, wherein the suitable solvent in step [A1] is a mixture of water and toluene, in a ratio from 10:1 to 1:10.
* * * * *